(12) United States Patent
Otsubo et al.

(10) Patent No.: US 6,666,851 B2
(45) Date of Patent: Dec. 23, 2003

(54) DISPOSABLE GARMENT

(75) Inventors: Toshifumi Otsubo, Kagawa-ken (JP); Yoshinori Kumasaka, Kagawa-ken (JP); Hiroyuki Soga, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 09/901,384

(22) Filed: Jul. 9, 2001

(65) Prior Publication Data

US 2002/0022814 A1 Feb. 21, 2002

(30) Foreign Application Priority Data

Jul. 31, 2000 (JP) ........................................ 2000-230679

(51) Int. Cl.[7] .......................... A61F 13/15; A61F 13/20; A41B 9/00

(52) U.S. Cl. ............................ 604/385.201; 604/396; 2/400

(58) Field of Search .................. 604/385.201, 393–402; 2/400–408

(56) References Cited

U.S. PATENT DOCUMENTS

| | | | | |
|---|---|---|---|---|
| 1,300,510 A | * | 4/1919 | Steele | 604/406 |
| 1,975,688 A | * | 10/1934 | Graves | 2/402 |
| 1,977,604 A | * | 10/1934 | Alsop | 604/401 |
| 2,024,134 A | * | 12/1935 | Anderson | 604/401 |
| 2,654,367 A | * | 10/1953 | Turnham | 604/401 |
| 3,552,736 A | * | 1/1971 | Frick et al. | 493/331 |
| 3,724,464 A | * | 4/1973 | Enlove | 604/385.201 |
| 3,774,610 A | * | 11/1973 | Eckert et al. | 604/385.201 |
| 3,782,714 A | * | 1/1974 | Spencer et al. | 493/250 |
| 3,848,595 A | * | 11/1974 | Endres | 604/385.201 |
| 3,884,234 A | * | 5/1975 | Taylor | 604/385.201 |
| 3,924,627 A | * | 12/1975 | Nystrand | 604/385.201 |
| 3,968,799 A | * | 7/1976 | Schrading | 604/385.201 |
| 4,037,602 A | * | 7/1977 | Hawthorne | 604/375 |
| 4,205,679 A | * | 6/1980 | Repke et al. | |
| 4,630,320 A | * | 12/1986 | Van Gompel | |
| 4,769,023 A | * | 9/1988 | Goebel et al. | 604/385.21 |
| 4,938,753 A | * | 7/1990 | Van Gompel et al. | 604/385.29 |

FOREIGN PATENT DOCUMENTS

| | | | | |
|---|---|---|---|---|
| AU | 640068 | * | 10/1991 | 604/396 |
| JP | 6-63072 | | 3/1994 | |
| JP | 6-63073 | | 3/1994 | |

* cited by examiner

Primary Examiner—K. M. Reichle
(74) Attorney, Agent, or Firm—Butzel Long

(57) ABSTRACT

A disposable garment that includes a crotch region. The crotch region has a pair of folding guides that extend transversely across a zone defined between peripheral edge portions of respective leg-openings and intersect each other in a transversely middle zone of the crotch region. The crotch region is tucked about the folding guides inwardly of the garment so that the crotch region may be divided by the folding guides into substantially triangular first and second zones defined between the peripheral edge portions of the respective leg-openings and the folding guides, respectively, a third zone extending from the folding guides into a front region, and a fourth zone extending from the folding guides into a rear region with the first and second zones being disposed between the third and fourth zones.

4 Claims, 7 Drawing Sheets

DISPOSABLE GARMENT

BACKGROUND OF THE INVENTION

This invention relates to a disposable garment adapted to absorb and to hold excretion discharged thereon.

Japanese Patent Application Publications Nos. 1994-63072A and 1994-63073A describe disposable diapers comprising front and rear waist regions separately prepared and placed upon each other and crotch regions partially defined by the front and rear waist regions. In the disposable diapers well known from the disclosures of the Publications, the front and rear waist regions are bonded together along bonding lines extending from said crotch region up- and outward to side edges of the waist regions to describe circular arcs so that the waist-opening is defined at an upper part and a pair of leg-openings are defined at a lower part of the diaper. Each of the front and rear waist regions comprises, in turn, a liquid-pervious topsheet, a liquid-impervious backsheet and a liquid-absorbent panel disposed between these two sheets. In the diapers well known from the disclosures of the Publications, the bonding lines curving up- and outward from the crotch region to the side edges of the waist regions enable the transverse dimension of the crotch region to be dimensioned relatively large.

However, the diapers well known from the disclosures of the foregoing Publications are disadvantageous in that, if the transverse dimension of the crotch region is larger than the corresponding dimension of the wearer's crotch region, the peripheral edge portions of the respective leg-openings may rub the inner sides of the wearer's thighs as the diaper is pulled up along the wearer's waist, thereby obstructing the diaper from being smoothly put on the wearer's body. To avoid this problem, the initial dimension of the crotch region may be appropriately reduced. However, the dimension of the core lying in the crotch region also must be reduced and this would inevitably require corresponding reduction of the core's dimension so that an excretion absorbing capacity achieved in the crotch region would also be deteriorated.

SUMMARY OF THE INVENTION

It is an object of this invention to provide a disposable garment that is designed so that the transverse dimension of the crotch region may be appropriately reduced and thereby the article may be smoothly put on the wearer's body without deterioration of the excretion absorbing capacity achieved in the crotch region.

According to this invention, there is provided a trunks-type or a briefs-type disposable garment comprising a front trunk region, a rear trunk region opposed to the front trunk region and a crotch region extending between these trunk regions so as to define a waist-opening at an upper part and a pair of leg-openings at a lower part of the trunks-type or a briefs-type disposable garment.

According to this invention, the crotch region has a pair of folding guides that extend transversely across a zone defined between peripheral edge portions of the respective leg-openings and intersect each other in a transversely middle zone of the crotch region. The crotch region is tucked about the folding guides inwardly of the article so that the crotch region is divided by the folding guides into substantially triangular first and second zones defined between the peripheral edge portions of the leg-openings and the folding guides, respectively, a third zone extending from the folding guides into the front trunk region, and a fourth zone extending from the folding guides into the rear trunk region with the first and second zones being disposed between the third and fourth zones.

According to one embodiment of this invention, the trunks-type or briefs-type disposable garment comprises a liquid-pervious topsheet, a liquid-impervious backsheet and a liquid-absorbent core disposed between these sheets and wherein the top- and backsheets as well as the core are folded about the folding guides in the first and second zones.

According to another embodiment of this invention, the garment maintains the first and second zones in the tucked-in shapes until the garment is actually used.

BRIEF DESCRIPTION OF THE DRAWINGS

FIG. 3 is a perspective view showing a diaper as the first and second zones are being tucked in;

FIG. 4 is a perspective view showing the diaper after the first and second zones have been tucked in;

FIG. 8 is a perspective view showing the diaper of FIG. 6 as the first and second zones are being tucked in; and FIG. 9 is a perspective view showing the diaper of FIG. 6 as the first and second zones have been tucked in.

DETAILED DESCRIPTION OF THE PREFERRED EMBODIMENTS

Details of a disposable garment according to this invention will be more fully understood from the description of the trunks-type disposable diaper and the briefs-type disposable diaper as embodiments given hereunder with reference to the accompanying drawings.

Figure 1:
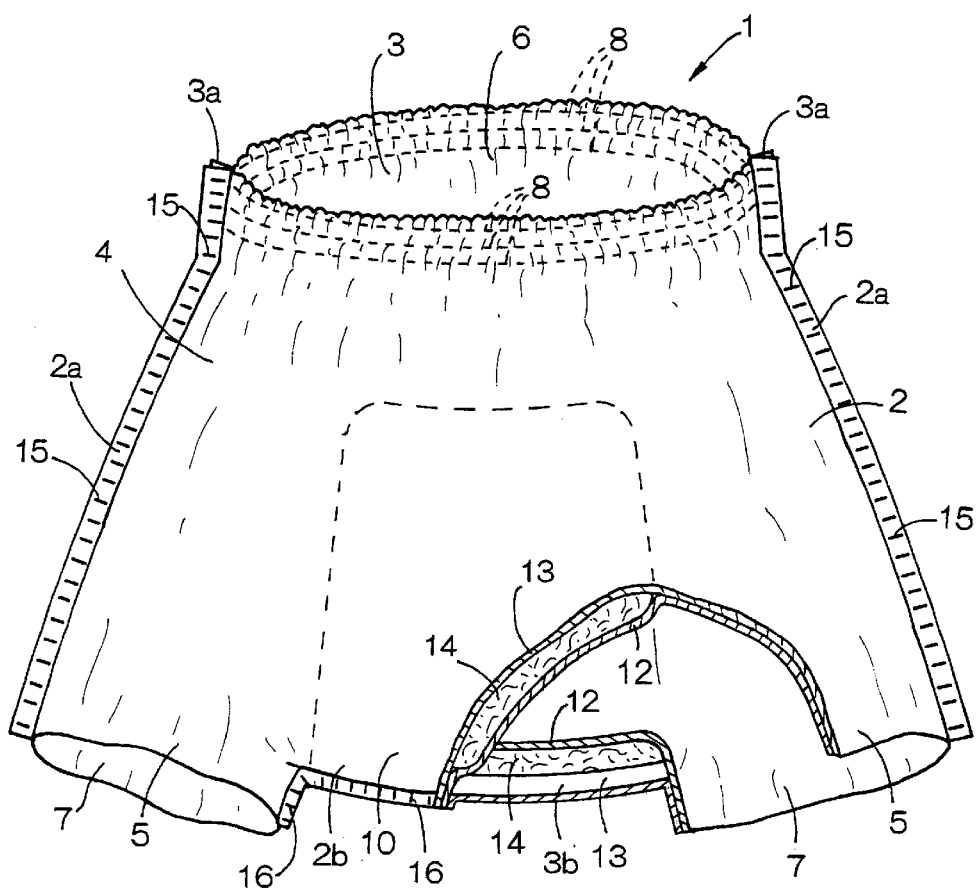
FIG. 1 is a perspective view showing a trunks-type disposable diaper according to this invention as partially broken away.
Figure 2:
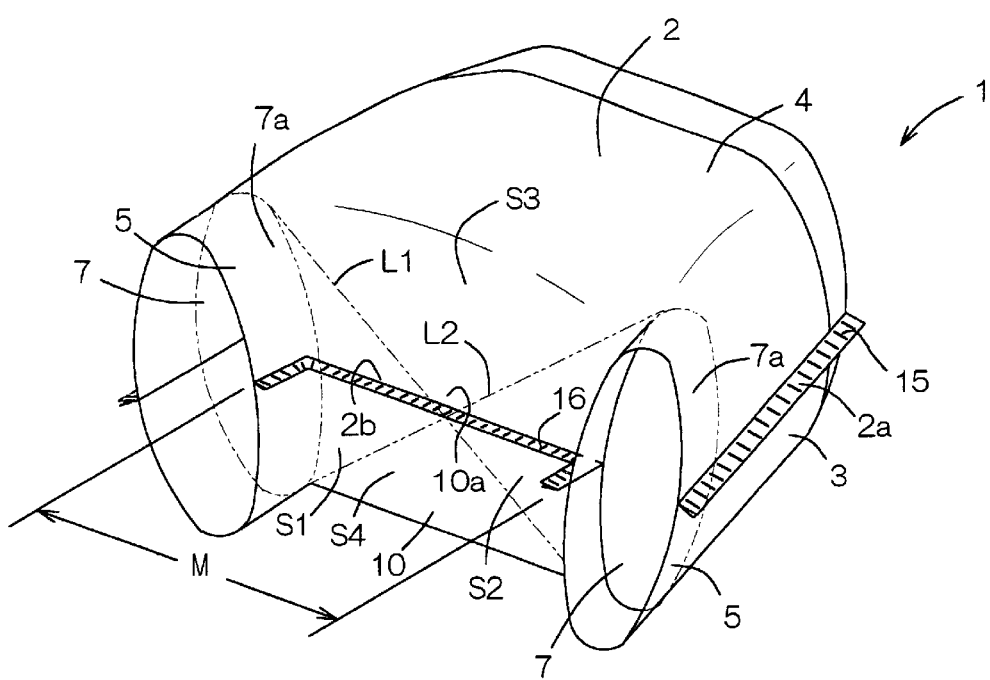
FIG. 2 is a perspective view showing a diaper as viewed from the side of the crotch region.

FIG. 1 is a perspective view showing a trunks-type disposable diaper 1 according to this invention as partially broken away and FIG. 2 is a perspective view schematically illustrating the diaper 1 as viewed from the side of the crotch region 10. The diaper 1 has a trunk body 4 formed by a front trunk region 2 and a rear trunk region 3 prepared separately of the front trunk region 2 to cover a wearer's torso and a pair of leg portions 5 formed by lower extensions of the front and rear trunk regions 2, 3 to cover the wearer's respective thighs. The diaper 1 is formed at an upper part of the trunk body 4 with a waist-opening 6 and at leg portions 5 with leg-openings 7. The leg portions 5 circumferentially extend downward to form peripheral edge portions 7a of the leg-openings 7.

The trunk body 4 has a crotch region 10 extending between the leg portions 5. An elastically stretchable member 8 comprising a plurality of circumferentially extending elements is attached to a peripheral edge of the waist-opening 6.

Each of the front and rear trunk regions 2, 3 comprises a liquid-pervious topsheet 12, a liquid-impervious backsheet 13 and a liquid-absorbent core 14 that is disposed between these two sheets 12, 13 and entirely covered with and bonded to water-pervious tissue paper (not shown). The core 14 is bonded to at least one of the top- and backsheets 12, 13 with the tissue paper therebetween. The elastic member 8 associated with the waist-opening is disposed between the top- and backsheets 12, 13 in the front and rear trunk regions 2, 3 and bonded under tension to at least one of these sheets 12, 13.

The front and rear trunk regions 2, 3 are put flat together along peripheral edge portions thereof and bonded together by a plurality of welding spots 15 intermittently arranged in the vicinity of transversely opposite side edge portions 2a, 3a of these trunk regions 2, 3 and additionally by a plurality of welding zones 16 arranged intermittently in the vicinity of lower ends 2b, 3b of the front and rear trunk regions 2, 3 extending into the crotch region 10.

In the crotch region 10, a pair of folding guides L1, L2 transversely extend across a zone defined between the peripheral edge portions 7a of the respective leg-openings 7. The pair of folding guides L1, L2 intersect each other in a transversely middle zone 10a of the crotch region 10, as indicated by two-dotted chain lines in FIG. 2. The leg-openings 7 herein described with reference to FIG. 2 are formed along a lower edge of the trunk body 4, as indicated by chain lines in FIG. 2 when the diaper 1 is not provided with the leg portions 5. The crotch region 10 is divided by the folding guides L1, L2 into substantially triangular first and second zones S1, S2 defined between the peripheral edge portions 7a and the folding guides L1, L2, respectively, a third zone S3 extending from the folding guides L1, L2 into the front trunk region 2, and a fourth zone S4 extending from the folding guides L1, L2 into the rear trunk region 3.

Figure 3:
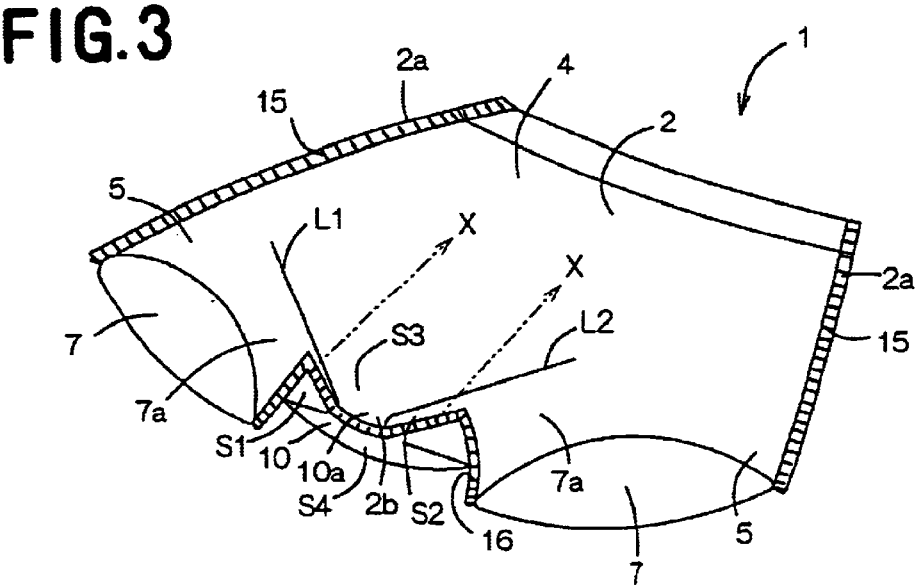
Figure 4:
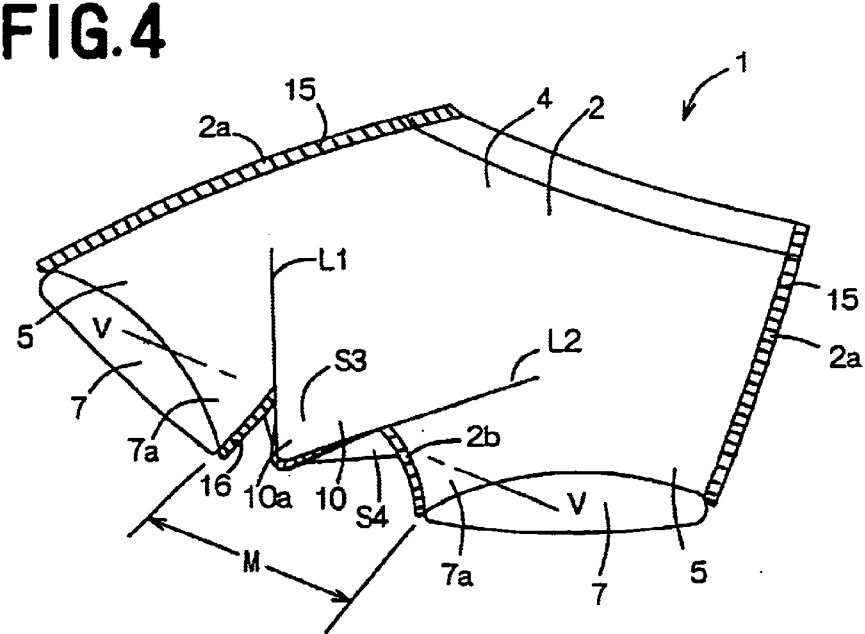
Figure 5:
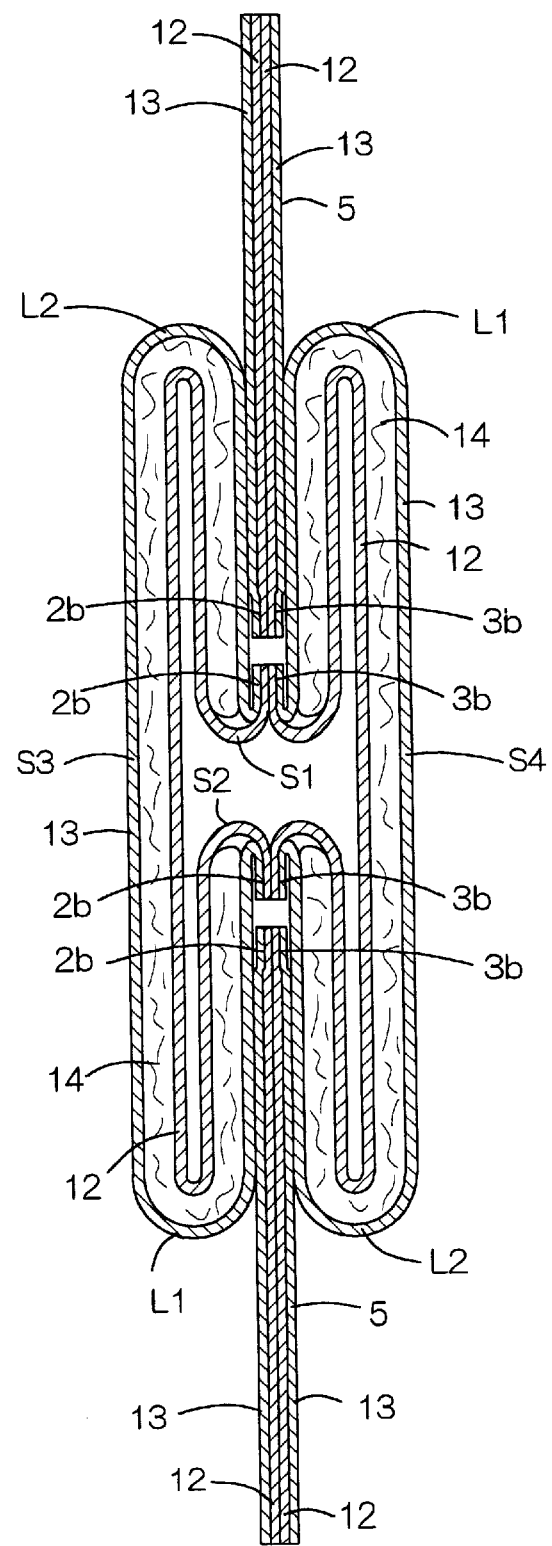
FIG. 5 is a sectional view taken along a line A—A in FIG. 4.

FIG. 3 is a perspective view showing the diaper as the first and second zones S1, S2 are being tucked in, FIG. 4 is a perspective view showing the diaper after the first and second zones S1, S2 have been tucked in and FIG. 5 is a sectional view taken along a line A—A in FIG. 4. FIGS. 3 and 4 illustrate how to tuck in the first and second zones S1, S2.

The diaper 1 is folded along the folding guides L1, L2 so that the first and second zones S1, S2 are tucked inwardly of the diaper 1 as indicated by an arrow X in FIG. 3. Referring to FIG. 4, the front and rear trunk regions 2, 3 are placed upon each other with the first and second zones S1, S2 disposed between the third and fourth zones S3, S4. In the diaper 1 having the first and second zones S1, S2 tucked in, a transverse dimension M of the crotch region 10 is smaller than the corresponding dimension M before the zones S1, S2 are tucked in (See FIG. 2).

With this diaper 1, the top- and backsheets 12, 13 and the core 14 are folded along the folding guides L1, L2 and thereby these top- and backsheets 12, 13 and core 14 are so firmly creased that said top- and backsheets 12, 13 as well as the core are not easily unfolded. In this way, the first and second zones S1, S2 are kept in their tucked shapes.

With this diaper 1, the initial transverse dimension of the crotch region 10 can be appropriately reduced by tucking in the first and second zones S1, S2 even if the initial transverse dimension M is larger than a transverse dimension of the wearer's crotch region. As a consequence, there is no anxiety that the peripheral edge portions 7a of the respective leg-openings 7 will rub the inner sides of the wearer's thighs as the diaper 1 is pulled up along the wearer's trunk. Accordingly, the diaper 1 can be smoothly put on the wearer's body.

The top- and backsheets 12, 13 and the core 14 are unfolded about the respective folding guides L1, L2 as the diaper 1 is pulled up along the wearer's trunk, and thus the first and second zones S1, S2 get out of their tucked-in shapes. Excretion absorbing capacity of the core 14 lying in the crotch region 10 is not affected by the unfolding of the first and second zones S1, S2 since the core 14 lying in the crotch region 10 is dimensionally constant.

Figure 6:
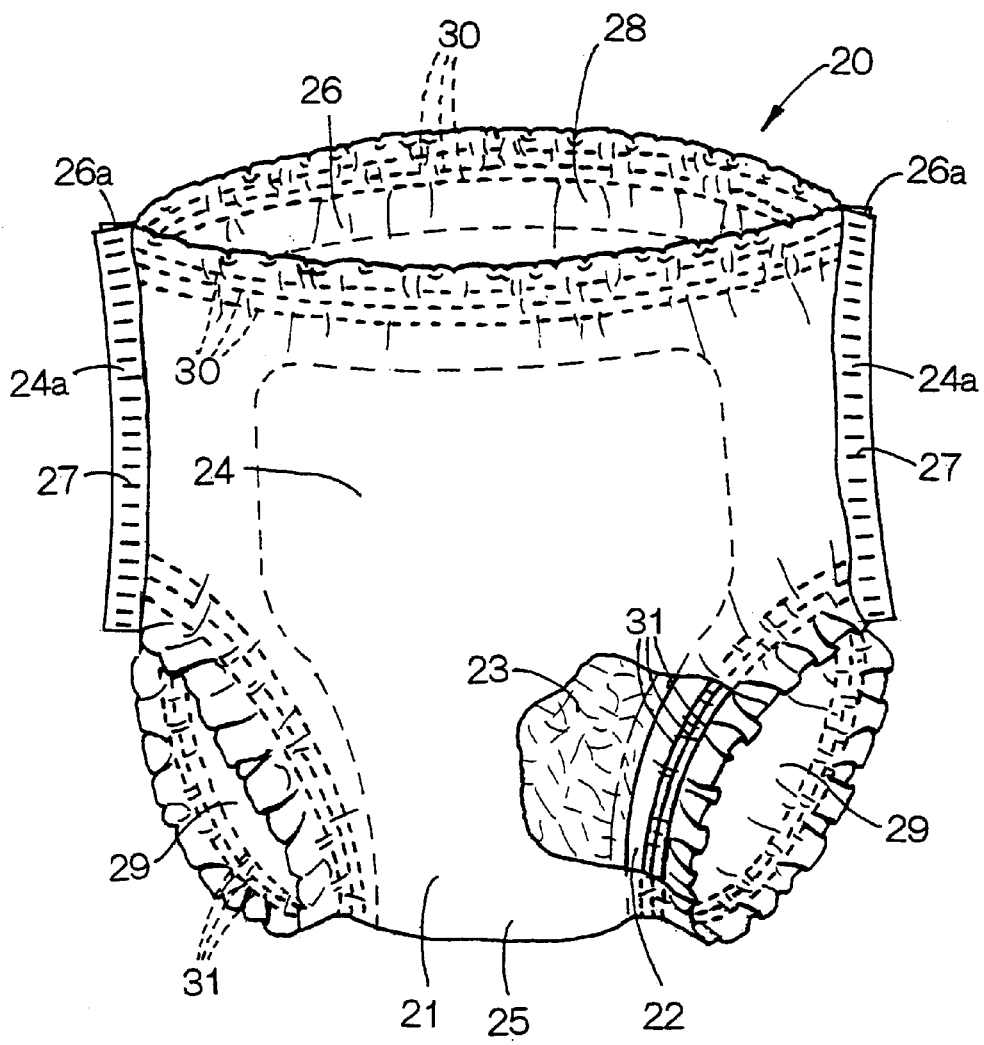
FIG. 6 is a perspective view showing a briefs-type disposable diaper as partially broken away.
Figure 7:
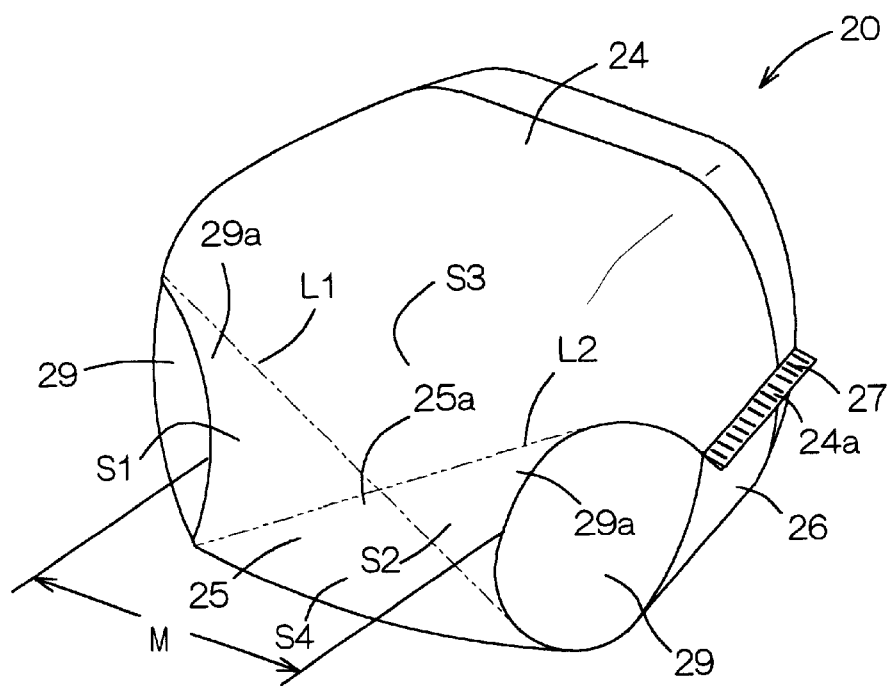
FIG. 7 is a perspective view showing the diaper of FIG. 6 as viewed from the side of the crotch region.
Figure 8:
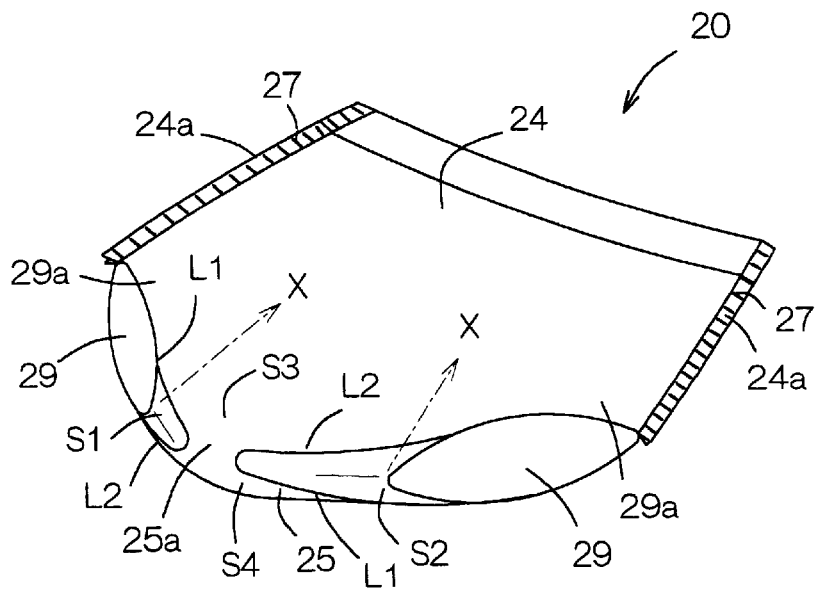
Figure 9:
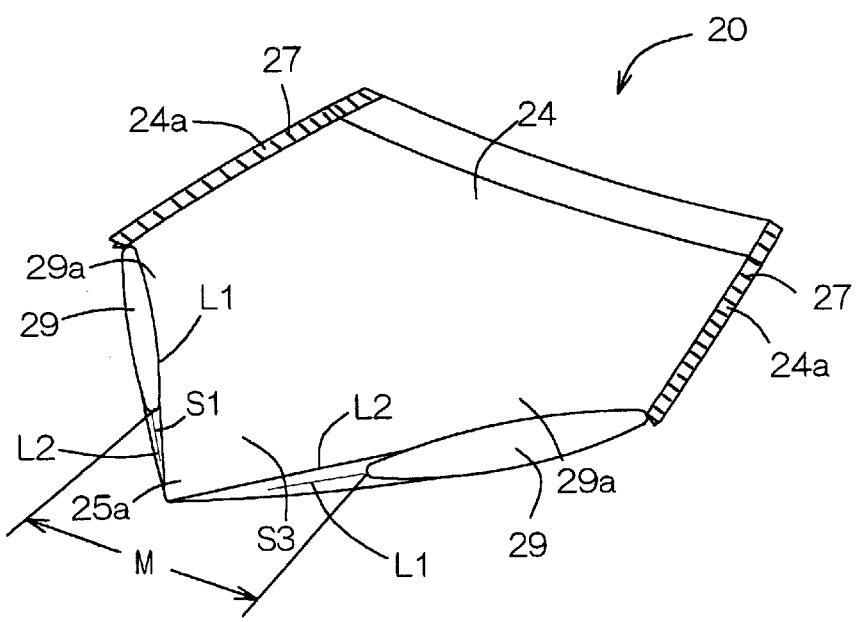

FIG. 6 is a perspective view showing a briefs-type disposable diaper 20 as partially broken away, FIG. 7 is a perspective view showing the diaper 20 as viewed from the side of the crotch region 25, FIG. 8 is a perspective view showing the diaper 20 as the first and second zones S1, S2 are being tucked in and FIG. 9 is a perspective view showing the diaper 20 after the first and second zones S1, S2 have been tucked in. FIGS. 7, 8 and 9 abstractly illustrate the diaper 20.

The diaper 20 comprises a liquid-pervious topsheet 22, a liquid-impervious backsheet 21 and a liquid-absorbent core 23 that is disposed between these two sheets 21, 22 and entirely covered with and bonded to water-pervious tissue paper (not shown). The core 23 is bonded to at least one of the top- and backsheets 22, 21 with the tissue paper therebetween.

The diaper 20 has a front region 24, a rear region 26 opposed to the front region 24 and a crotch region 25 extending between these regions 24, 26. Transversely opposite side edge portions 24a, 26a of the front and rear regions 24, 26 of diaper 20 are put flat and bonded together by a plurality of welding spots 27 intermittently arranged along the transversely opposite side edge portions 24a, 26a so as to define a waist-opening 28 and a pair of leg-openings 29.

A circumferentially extending elastic member 30 comprising a plurality of elements is disposed along a peripheral edge portion of the waist-opening 28 between the top- and backsheets 22, 21 and bonded under tension to at least one of these sheets 21, 22. Similarly, circumferentially extending elastic members 31 each comprising a plurality of elements are disposed along peripheral edge portions of the respective leg-openings 29 between the top- and backsheets 22, 21 and bonded under tension to at least one of these two sheets 21, 22.

A pair of folding guides L1, L2 transversely extend across a zone defined between the peripheral edge portions 29a of the respective leg-openings 29 in the crotch region 25 of diaper 20 and intersect each other in a transversely middle zone 25a of the crotch region 25, as in the case of the embodiment shown in FIG. 1. The crotch region 25 is divided by the folding guides L1, L2 into substantially triangular first and second zones S1, S2, a third zone S3 extending from the folding guides L1, L2 into the front region 24, and a fourth zone S4 extending from the folding guides L1 and L2 into the rear region 26.

When the diaper 20 is folded along the folding guides L1, L2, the first and second zones S1, S2 are tucked inwardly of the diaper 20 as indicated by an arrow X in FIG. 8. Referring to FIG. 9, the front and rear regions 24, 26 are placed upon each other with the first and second zones S1, S2 disposed between the third and forth zones S3, S4. When the first and second zones S1, S2 are tucked in, a transverse dimension M of the crotch region 25 is smaller than the corresponding dimension M before the zones S1, S2 are tucked in (See FIG. 7).

The embodiments of the diaper 1, 20 as illustrated, may be individually packaged with the first and second zones S1, S2 tucked inwardly of the diaper 1, 20. Alternatively, a plurality of diapers 1, 20 maybe packaged in the form of a stack with the first and second zones S1, S2 of each diaper 1, 20 tucked inwardly of the diaper.

The topsheet 12, 22 may be formed from a liquid-pervious sheet such as a nonwoven fabric or porous plastic film, and preferably from a liquid-pervious hydrophilic sheet. The backsheet 13, 21 may be formed from a hydrophobic nonwoven fabric, a liquid-impervious plastic film or a laminated sheet of hydrophobic nonwoven fabric and a plastic film, and preferably from a breathable but liquid-impervious sheet. It is also possible to form the backsheet 13, 21 from a composite nonwoven fabric (SMS nonwoven fabric) consisting of a melt blown nonwoven fabric having a high water-resistance and two layers of spun bond nonwoven fabric having high strength and flexibility sandwiching the melt blown nonwoven fabric.

The nonwoven fabric may be selected from the group including spun lace-, needle punch-, melt blown-, thermal bond-, spun bond-, chemical bond- and air throughnonwoven fabric. Component fiber of the nonwoven fabric may be selected from the group including polyolefine-, polyester- and polyamide-based fibers and polyethylene/ polypropylene or polyethylene/polyester core-sheath type conjugated fiber and side-by-side-type conjugated fiber.

The core 14, 23 is a mixture of fluff pulp, high absorption polymer grains and thermoplastic synthetic resin fiber compressed to a desired thickness. The high absorption polymer may be selected from the group including starch-, cellulosebased polymer and synthetic polymer.

Bonding of the top- and backsheets 12, 22, 13, 21 and the core 14, 23 as well as attaching of the elastic member 8, 30, 31 may be carried out using a suitable adhesive such as a hot melt adhesive or a welding technique such as sonic sealing or heat-sealing.

In the disposable garment according to this invention, the first and second zones of the crotch region are tucked about the respective folding guides inwardly of the garment so that the first and second zones are divided by the folding guides and may be disposed between the third and fourth zones of the crotch region. The transverse dimension of the crotch region can be thereby reduced with respect to the corresponding dimension before the first and second zones are tucked in. As a consequence, there is no anxiety that the peripheral edge portions of the respective leg-openings will rub the inner sides of the wearer's thighs as the diaper is pulled up along the wearer's trunk. Accordingly, the diaper can be smoothly put on the wearer's body.

The excretion absorbing capacity of the core in the crotch region is not affected by reduction of the crotch region's transverse dimension due to tucking-in of the first and second zones. This is because a transverse dimension of the core lying in the crotch region is not affected by such reduction of the crotch region's transverse dimension.

What is claimed is:

1. A trunks-type disposable garment having a trunk body and further comprising:

a front trunk region;

a rear trunk region opposed to said front trunk region;

a crotch region extending between said front and rear trunk regions;

a waist-opening at an upper part of said trunk body;

a pair of leg-openings at a lower part of said trunk body, said front and rear trunk regions being bonded along transversely opposite side edge portions thereof to define said waist-opening and said pair of leg-openings; and a pair of folding guides provided in said crotch region, said pair of folding guides transversely extending across a zone defined between peripheral edge portions of the leg-openings and intersecting each other in a transversely middle zone of said crotch region, said crotch region being tucked about folding guides inwardly so that said crotch region is divided by said folding guides into substantially triangular first and second zones defined between said peripheral edge portions of said leg-openings and said folding guides, respectfully, a third zone extending from said folding guides into said front trunk region, and a fourth zone extending from said folding guides into said rear trunk region with said first and second zones being disposed between said third and fourth zones so that the crotch region defines an inverter triangle between the pair of leg-openings.

2. The disposable garment according to claim 1, further comprising:

a liquid-pervious topsheet;

a liquid-impervious backsheet; and a liquid-absorbent core disposed between said liquidpervious topsheet and said liquid-impervious backsheet, said liquid-pervious topsheet, said liquid-impervious backsheet and said core being folded about said folding guides in said first and second zones.

3. A briefs-type disposable garment having a body and further comprising:

a front region;

a rear region opposed to said front region;

a crotch region extending between said front and rear regions;

a waist-opening at an upper part of said body;

a pair of leg-openings at a lower part of said body, said front and rear regions being bonded along transversely opposite side edge portions thereof to define said waist-opening and said pair of leg-openings; and a pair of folding guides provided in said crotch region, said pair of folding guides transversely extending across a zone defined between peripheral edge portions of the leg-openings and intersecting each other in a transversely middle zone of said crotch region, said crotch region being tucked about folding guides inwardly so that said crotch region is divided by said folding guides into substantially triangular first and second zones defined between said peripheral edge portions of said leg-openings and said folding guides, respectfully, a third zone extending from said folding guides into said front region, and a fourth zone extending from said folding guides into said rear region with said first and second zones being disposed between said third and fourth zones so that the crotch region defines an inverter triangle between the pair of leg-openings.

4. The disposable garment according to claim 3, further comprising:

a liquid-pervious topsheet;

a liquid-impervious backsheet; and a liquid-absorbent core disposed between said liquidpervious topsheet and said liquid-impervious backsheet, said liquid-pervious topsheet, said liquid-impervious backsheet and said core being folded about said folding guides in said first and second zones.

* * * * *